United States Patent [19]
Goor et al.

[11] Patent Number: 4,798,211
[45] Date of Patent: Jan. 17, 1989

[54] DIAGNOSTIC METHODS AND APPARATUS EMPLOYING MONITORING OF MYOCARDIAL ISCHEMIA

[76] Inventors: Daniel Goor, Rehov David Hemelech 47, Tel Aviv; Raphael Mohr, Rehov Hameshorer 10, Kiryat Krinitzi, Ramat Gan, both of Israel; Ihsan A. Haddad, 375 Lexington Rd., Concord, Mass. 01742; William R. Oliver, 13 Country Club Dr., Chelmsford, Mass. 01824

[21] Appl. No.: 856,502

[22] Filed: Apr. 25, 1986

[51] Int. Cl.$^4$ .............................................. A61B 5/02
[52] U.S. Cl. .................................... 128/668; 128/673
[58] Field of Search ................ 604/344; 128/713, 668, 128/671–675, 691–694, 700

[56] References Cited

U.S. PATENT DOCUMENTS 4,429,701  2/1984  Goor et al. ........................... 128/713

OTHER PUBLICATIONS

Sheppard, L. G., "Surgical IC Automation", JAAMF, v. 6, #1, Jan.-Feb. 1972, pp. 74–78.
Sibbald, W. J., editor, "Critical Care Clinics: Symposium on Cardiovascular Crises in the Critically Ill", W. B. Saunder & Co., vol. 1, No. 3, 11/1985, pp. 445–451, 508–511, 535–546.
Simpson, J. B. et al., "A New Cathetic System for Coronary Angioplasty", Amer. Jrnl. of Cardiology, 4/1/82, pp. 1216–1222.

*Primary Examiner*—Francis J. Jaworski
*Attorney, Agent, or Firm*—Hale and Dorr

[57] ABSTRACT

A method and apparatus monitor myocardial ischemic events in various medical applications for providing continuous and contemporaneous information regarding, for example, modifying the amount of medication for a patient, determining response during (PTCA) balloon angioplasty, monitoring the onset of myocardial ischemic events during induction of anesthesia, determining painless myocardial ischemia in a resting patient, and monitoring the onset of myocardial ischemic during stress conditions in a patient. The method and apparatus also provide a calibration method for determining from a Resistive Index and using the resulting transformation for calculating, on a continuing basis, both systemic vascular resistance and cardiac output.

13 Claims, 1 Drawing Sheet

DIAGNOSTIC METHODS AND APPARATUS EMPLOYING MONITORING OF MYOCARDIAL ISCHEMIA

BACKGROUND OF THE INVENTION

The present invention relates to a method and apparatus for monitoring of myocardial ischemia, and in particular for monitoring myocardial ischemia during (a) the induction of anesthesia, (b) PTCA Balloon Angioplasty, (c) stress, and (d) drug administration, and for the determination and calculation of Systemic Vascular Resistance and Cardiac Output.

Myocardial ischemia can be defined as a decreased supply of blood to the heart, and more precisely as an imbalance between the myocardial oxygen supply and demand. In most clinical situations, the reason for this imbalance is inadequate perfusion (blood injection) of the myocardium (muscle tissue of the heart) due to obstructions or stenosis (a narrowing) of the coronary arteries (the arteries that supply blood to the heart). The ischemia can last only a few seconds or it can persist for minutes or even hours, causing transient or permanent damage to the heart muscle (myocardial infarction). Myocardial ischemia is usually accompanied by chest pain (angina). In many cases, however, it is not accompanied by pain, or the subject is not aware of the pain, for example, when the subject is unconscious, and therefore detection of the ischemia must be made by objective methods rather than by relying on complaints of the subject.

The most commonly used objective criteria for ischemia detection and monitoring are the electrocardiographic (ECG) changes at rest or during effort testing. Ischemia can be demonstrated by the elevation or depression of the S-T segment, by inversion or other changes in T-waves, or by changes in the shape or width of the QRS complex. However, sometimes electrocardiographic changes are not detected because the appropriate electrocardiograph lead (of the 12 commonly used leads) is not being monitored. At other times, the electrocardiograph is too sensitive and reflects changes that have no real significance.

For these reasons, methods other than use of the ECG, are employed to detect myocardial ischemia. These other methods include:

a. Hemodynamic Changes Associated with Ischemia.—Ischemia can be associated with elevation or depression of the subject's blood pressure. Blood pressure can therefore also be used for continuously monitoring for myocardial ischemia. This method is commonly used in operating rooms; and it is good cardiac anesthesia practice to prevent increases and decreases of blood pressure as much as possible. However, changes in blood pressure can result from pain or from reasons; and therefore, changes in blood pressure alone are unreliable as the primary indicator of ischemia.

Another commonly used hemodynamic parameter is the pressure in the left atrium. This parameter can be monitored indirectly, for example, by using a Swann-Ganz catheter which measures the pulmonary-capillary wedge pressure that is usually equal to the left atrial pressure. Left atrial pressure can also be measured directly after open heart procedures through a catheter introduced into the left atrium. In catheterization laboratories, the left ventricular end diastolic pressure (LVEDP) can be measured through a catheter introduced through the aorta. Changes in left atrial pressure usually reflect changes in LVEDP, and ischemia is usually associated with increased LVEDP. Because of the highly invasive nature of the pressure measurements of the left atrium, pulmonary-capillary wedge, or of the left ventricle, these methods are used only in special situations. It is also important to note that ischemia is not always associated with increased LVEDP.

b. Two-Dimensional Echocardiography—Important changes in ventricular wall motions or in ventricular dimensions are associated with ischemia. Two-dimensional echocardiography, using external transducers, can detect increased left ventricular end diastolic and end systolic volume. A trans-esophageal echocardiographic transducer allows continuous detection and monitoring of changes in ventricular wall motion, and therefore also enables monitoring of ischemia.

c. Radionuclide Ventriculography—Injection of radioactive marker (Tc-99n phyrophosphate stanus) that adheres to the myocardial muscle provides a method for monitoring changes in ventricular wall motion, and therefore also enables detection of ischemia. This method for the non-invasive detection of ischemia is used during rest and effort tests.

d. Thalium 201H perfusion scans provide a further method for the selective and non-invasive monitoring of the blood supply to the heart. Although radionuclide ventriculography and Thalium perfusion scans can detect ischemia, they both involve large and expensive instruments, and therefore these methods are not commonly used for monitoring of ischemia.

Objects of the invention are monitoring a patient during the induction of anesthesia, quantification of the extent of ischemic response during (PTCA) balloon angioplasty, monitoring a resting patient, monitoring stressed patients, monitoring ischemic events during drug medication, and calculating values of systemic vascular resistance and cardiac output in a reliable, convenient, and effective manner.

SUMMARY OF THE INVENTION

In accordance with the invention, a patient is monitored for his arterial pressure using, for example, an in-dwelling catheter, transducer, or pressure monitor. An apparatus takes the analog output from the pressure amplifier of the monitor and processes it for either a Resistive Index or systemic vascular resistance. The Resistive Index is a relative value and has no units of measure. Each patient requires the apparatus to be set or calibrated to an arbitrary "value," depending upon the patient, if systemic vascular resistance is to be displayed. Relative changes in the Resistive Index, however, do represent changes in ischemic condition and, in particular, increases in value of the measure can represent myocardial ischemic events.

The invention relates generally to monitoring the myocardial ischemia of a subject for determining one of several physical events relating to the subject or for determining systemic vascular resistance and cardiac output. In one aspect, the method features monitoring the onset of myocardial ischemic events during the induction of anesthesia. The use of the apparatus described herein (hereafter designated a "Resistometer") provides a Resistive Index corresponding to systemic vascular resistance, or the value of systemic vascular resistance (SVR) itself. In either instance, there is provided a digital value whose change is easily recognized.

In many instances, the change in the digital value appears before changes in the ECG can be detected.

In another aspect of the invention, the method measures the Resistive Index or SVR to determine quantification of the extent of ischemic response during (PTCA) balloon angioplasty. At present, there exists no method of quantification for the ischemic event that occurs during balloon inflation. The Resistive Index, as measured by the apparatus (the preferred apparatus being the Resistometer) will provide a numerical digital value for quantification of the event which will be proportional to the degree of myocardial ischemia which has developed.

In yet another aspect of the invention, the method and apparatus feature monitoring the onset of painless myocardial ischemia in a resting subject. While Holter ECG monitoring is considered the accepted method for detecting myocardial ischemic events in the resting or ambulatory patient, these recordings must be scanned by an instrument designed to recognize myocardial ischemic changes in the ECG. The Resistometer and method of the present invention produces a digital value which is immediately recognizable as above or below a predetermined base line value in the event that a myocardial ischemic change occurs.

The invention is further directed to a method and apparatus for monitoring the onset of myocardial ischemia during stress of a subject. ECG changes are typically the basis for diagnosing myocardial ischemic events during stress. This procedure, however, suffers the same disadvantages noted above with respect to monitoring the onset of painless myocardial ischemia in the resting patient. Accordingly, therefore, the Resistometer of the present method and apparatus will display an increase in value prior to noticeable changes in the corresponding ECG.

In yet a further aspect of the invention, the method and apparatus monitor the level of myocardial ischemic events for determining that drug dose level which inhibits occurrence of the events. It has been reported that up to eighty percent of the myocardial ischemic events which are experienced are painless, and that those subjects are therefore unaware of their occurrence. Holter monitoring, after scanning, will pinpoint those episodes; however, the Resistometer will display an increased digital value which can be easily recognized at the actual time of the event, thereby enabling a patient to modify, and in particular, to increase, his medication at that time.

The invention further provides a method and apparatus for calculating, from the Resistivity Index value, the systemic vascular resistance and cardiac output (CO) for the patient. In accordance with this method, the Resistometer apparatus is calibrated using a different known method for determining the value of cardiac output. Thereafter, the Resistometer, through its output Resistivity Index reading, will follow and read directly the cardiac output and systemic vascular resistance as is well known in the art. The Resistometer thus provides, contemporaneous with the event, an indication of any changes in the patient's systemic vascular resistance or cardiac output and provides those values for use by, for example, a physician.

In accord with a preferred embodiment of the invention, a non-invasive sensor is desirable to provide a blood pressure measurement for determining the Resistive Index. This would provide application of the method and apparatus outside of the hospital, clinic, or laboratory environment.

The systemic vascular resistance (SVR) of a subject is the total peripheral resistance (TPR) of the subject's cardiovascular system. Measurements of the subject's systemic vascular resistance, together with other measurements, are commonly made in order to assess the status of the subject's cardiovascular system, particularly in monitoring post-operation recovery of patients. Some of the other measurements presently made in assessing the status of the subject's cardiovascular system include the mean arterial pressure (MAP), central venous pressure (CVP), and cardiac output (CO). All these measurements have the following relationship:

$$MAP - CVP = CO \times SVR$$

This relationship will be recognized as the cardiovascular equivalent of Ohm's law of electricity, $E(\text{voltage}) = I(\text{current}) \times R(\text{resistance})$.

A number of techniques are known for measuring systemic vascular resistance. Particularly good results have been obtained when the method described in our U.S. Pat. No. 4,429,701, the disclosure of which is incorporated herein, in its entirety, the following steps:

A. detecting the arterial pressure of the subject and generating in response thereto a blood pressure signal having a waveform in accordance with the detected arterial pressure;

B. differentiating the blood pressure signal to produce a dP/dt signal having a waveform varying in accordance with the rate at which the blood pressure signal varies;

C. detecting the peak of the dP/dt signal to determine the peak dP/dt;

D. determining a value which is substantially equal to the arterial pressure at the time of said peak dP/dt and;

E. dividing said latter value by the peak dP/dt signal, which thereby produces a measurement corresponding to the systemic vascular resistance of the cardiovascular system.

Myocardial ischemia can be detected accurately when using only one channel, rather than the two channels described in the above-cited patent specification. It has also been found that the radial artery is too sensitive, and that best results are obtained when using a centrally located artery, preferably the femoral artery.

While invasive techniques have produced excellent results, it is considered that a non-invasive technique, such as using pressure cuffs, can also be used for monitoring the systemic vascular resistance in order to detect myocardial ischemia in accordance with the above method and apparatus.

BRIEF DESCRIPTION OF THE DRAWINGS

Other objects, features and advantages of the invention will be apparent from the following description, with reference to the accompanying drawings, in which.

DESCRIPTION OF A PREFERRED EMBODIMENT

Figure 1:
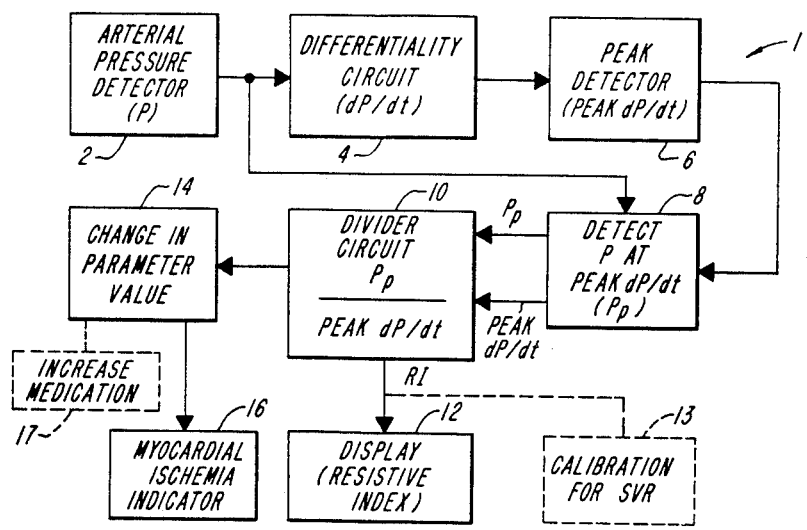
FIG. 1 is a block diagram illustrating a preferred apparatus constructed in accordance with the invention for detecting myocardial ischemia.

Referring to FIG. 1, a Resistometer system 1 monitors the Resistive Index and hence systemic vascular resistance of a subject in accordance with the method and apparatus described in U.S. Pat. No. 4,429,701 which is incorporated herein by reference. Briefly, the system includes an arterial pressure detector 2 detecting the blood-pressure (P) of the subject and generating in response thereto a blood-pressure signal having a waveform in accordance with the detected arterial pressure; a differentiating circuit 4 differentiating the blood-pressure signal (P) to produce a signal (dP/dt) having a waveform varying in accordance with the rate at which the blood-pressure signal (P) varies; a peak detector circuit 6 detecting the peak of the dP/dt signal and producing a corresponding signal (peak dP/dt); a circuit 8 for determining a value ($P_P$) which is substantially equal to the arterial pressure at the time of the peak dP/dt signal; and a divider circuit 10 for dividing the latter value ($P_P$) by the (peak dP/dt) signal. The output of circuit 10 is a value, hereinafter the "Resistive Index" (RI), which corresponds to the systemic vascular resistance (SVR) of the subject's cardiovascular system. Generally: $SVR = a + bRI$ where "a" and "b" are constants. The Resistive Index, so determined, is displayed in a display unit 12.

Circuit 8, which determines a value substantially equal to the arterial pressure at the time of the peak dP/dt signal, can detect the actual arterial pressure at the time of the peak dP/dt, or can detect merely the diastolic pressure, since the diastolic pressure is substantially equal to the arterial pressure at the time of the peak dP/dt. Further particulars with respect to the apparatus and method illustrated in FIG. 1 for measuring the systemic vascular resistance are described in the above-identified U.S. Pat. No. 4,429,701.

In accordance with the illustrated embodiment of the invention, the apparatus of FIG. 1 provides, at the display 12, as noted above, a measure of "Resistive Index." The value of the Resistive Index, in accordance with the illustrated embodiment of the invention and U.S. Pat. No. 4,429,701, corresponds to a measure of the systemic vascular resistance. The Resistive Index, as defined herein, is the ratio of diastolic pressure, at the time when the change in diastolic pressure is at its peak, to the peak value of the derivative of the pressure. This relationship is described in greater detail in the above-identified United States patent.

In order to relate, on a continuing basis, the value of Resistive Index to systemic vascular resistance, in accordance with the claimed invention, the apparatus and method provide at 13 for calibrating the apparatus by measuring the cardiac output and hence the systemic vascular resistance in accordance with a separate, known method, and at two operating points for a particular subject. This provides the proportionality constant "b" and offset constant "a," defined above, and enables one to calibrate the RI output of the apparatus of FIG. 1 so that the resulting value on display 12 can directly read the systemic vascular resistance and cardiac output for the subject, if desired.

By monitoring then the digital value displayed at display 12, whether it represents systemic vascular resistance or Resistive Index, one can determine, for example, the onset of myocardial ischemic events during the induction of anesthesia in a patient. This typically occurs during surgery in coronary patients. The Resistive Index from display 12 provides a digital value whose change is easily recognized, for example electronically using a circuit 16. In many instances, the change in Resistive Index appears before the corresponding changes in the ECG can be detected.

In another aspect, the digital reading of display 12 relates directly to quantification of the extent of the myocardial ischemic response during percutaneous transluminal angioplasty (PTCA). This provides for the detection and relative quantification of the myocardial ischemic event. At present there is no method of quantification for the ischemic event which occurs during balloon inflation. The Resistive Index provides a numerical value for quantification of the event which is, it is considered, proportional to the degree of the myocardial ischemia developed.

In yet another aspect, the digital value of Resistive Index at display 12 provides for monitoring the onset of a painless myocardial ischemia in a resting patient. This continuous monitoring of, for example, hospitalized patients with, for example, myocardial infarcts and other types of unstable angina pectoris, is significantly better than the accepted method of detection of myocardial ischemic events in the resting or ambulatory patient by Holter ECG monitoring. These recordings must be scanned by an instrument designed to recognize myocardial ischemic changes in the ECG. The Resistive Index, on the other hand, provides a digital value which is immediately recognizable as being above or below a predetermined base line in the event that an ischemic change occurs.

The digital value output of the apparatus at display 12 also allows for a method of monitoring the onset of myocardial ischemia during stress, and in particular for screening in specific stress tests where one is detecting the angina pectoris. Such changes can be determined, for example, by evaluating the ECG and diagnosing the ischemic events during the stress test. The Resistive Index, however, provides a display which will increase in value prior to noticeable changes in the ECG.

The Resistive Index or the corresponding value of systemic vascular resistance, provided by display 12 is also advantageous for determining drug dose levels which will inhibit the occurrence of myocardial ischemic events. In particular, the method provides for monitoring by means 14 the Resistive Index available from divider 10 and alerting the patient to increase his medication (or automatically increasing medication by means 17) at a time when the systemic vascular resistance or the Resistive Index increases. This value is easily recognizable since it is presented as a digital value.

Figure 2:
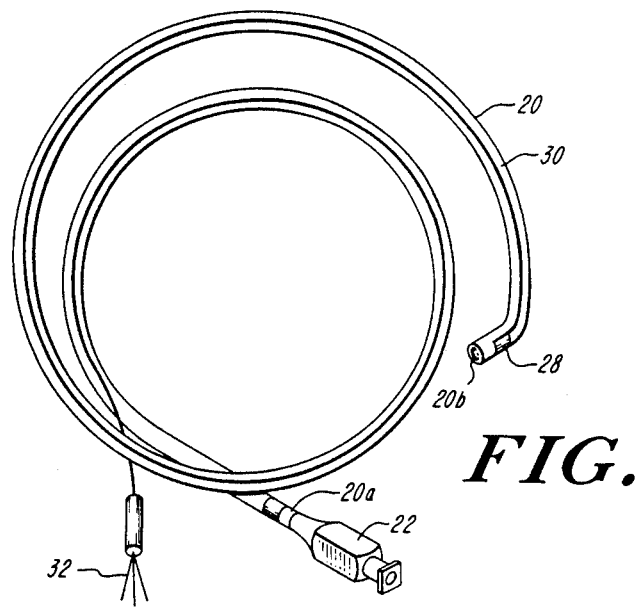
FIG. 2 illustrates a flexible catheter tube particularly useful with the apparatus of FIG. 1.
Figure 3:
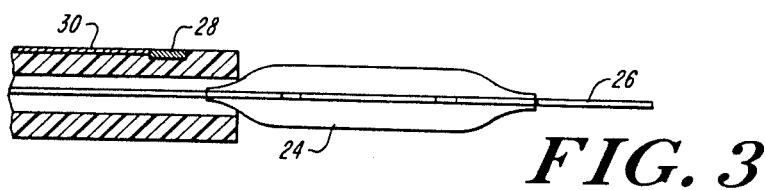
FIG. 3 is an enlarged fragmentary view illustrating the use of a coronary balloon dilatation catheter with the catheter tube of FIG. 2.

FIGS. 2 and 3 illustrate a device particularly useful for the arterial pressure detector 2 of FIG. 1 for measuring the arterial blood pressure (P).

The illustrated device includes a flexible catheter tube 20 insertable into the artery of the subject. A fitting 22 is carried at a proximal end 20a of the catheter tube 20 for the insertion of a coronary balloon dilatation catheter 24 (FIG. 3) using a guide wire 26. The wall at a distal tip 20b of catheter tube 20 has embedded therein a micro-manometer 28, that is, a pressure transducer for measuring the blood-pressure and for outputting the electrical signal P corresponding to the detected arterial pressure. Electrical leads 30 leading from connectors 32 at the proximal end 20a of catheter tube 20 to micromanometer 28 are also embedded within the wall of the catheter tube 20.

Referring to FIG. 3, micro-manometer 28 is embedded in the wall of catheter tube 20 so that the outer face of the micro-manometer is directly exposed to the blood in the artery, and so that the inner face of the embedded micro-manometer is covered by the inner face of the wall of the catheter tube 20. Thus, micromanometer 28 directly senses the blood pressure on the outer face of the micro-manometer, and generates the electrical signal P representing a precise measurement of the arterial blood pressure, which electrical signal is transmitted through leads 30 and connectors 32 to the differentiating circuit 4 of FIG. 1.

The balloon dilatation catheter 24, illustrated in FIG. 3, is used particularly when there is an obstruction in the coronary artery. When so used, the flexible catheter tube 20 is first inserted into the artery to bring its distal end 20b to the ostium of the coronary artery. The balloon dilatation catheter 24 is inserted through the catheter tube to the point of the obstruction, whereupon the balloon is inflated to dilate the coronary artery at the place of the obstruction. During this procedure, the arterial pressure is continuously detected by micro-manometer 28 add is used for continuously monitoring the systemic vascular resistance in accordance with the abovedescribed method as illustrated in FIG. 1. A precise measurement of the arterial pressure for this purpose is produced because the micro-manometer 28 is embedded in the outer face of the catheter tube 20 so as to be exposed to the blood in the artery. This permits a more precise detection of the blood pressure, since the micro-manometer is not significantly influenced by the inflation of the balloon in catheter 24.

Myocardial monitoring and detection is described above with respect to an invasive procedure, involving, for example, heart catheterization or balloon angioplasty dilatation of the coronary arteries. While this is a preferred procedure, ischemia monitoring and detection can also be performed in accordance with the present invention using a non-invasive procedure, such as by the use of pressure cuffs. Also, while the described technique monitors the Resistive Index, and hence systemic vascular resistance, in accordance with the method and apparatus described in our U.S. Pat. No. 4,429,701, it will be appreciated that other methods for monitoring systemic vascular resistance can also be used.

Other variations, modifications and applications of the invention will be apparent to those practiced in the field and are within the scope of the following claims.

What is claimed is:

1. A method for monitoring the onset of a myocardial ischemic event during the induction of anesthesia in a subject comprising the steps of
monitoring values of a parameter corresponding to systemic vascular resistance of the subject, and
detecting the onset of myocardial ischemic events during the induction of anesthesia when said monitored parameter value changes in accordance with a selected numerical amount.

2. The method according to claim 1 wherein said parameter monitoring step comprises the steps of:
   A. detecting the arterial pressure, P, of the subject and generating in response thereto a blood pressure signal having a waveform in accordance with the detected arterial pressure;
   B. differentiating said blood pressure signal to produce a dP/dt signal having a waveform varying in accordance with the rate at which the blood pressure signal varies;
   C. detecting the peak of said dP/dt signal to determine the peak dP/dt;
   D. determining a value which is substantially equal to the arterial pressure at the time of said peak DP/dt; and
   dividing said latter value by said peak dP/dt signal, which thereby produces a measurement of the parameter corresponding to the systemic vascular resistance of said subject's cardiovascular system.

3. A method for quantifying the extent of myocardial ischemic response during (PTCA) balloon angioplasty of a subject comprising the steps of
monitoring values of a parameter corresponding to systemic vascular resistance of the subject, and
detecting when said parameter value changes by a selected numerical value for indicating the degree of myocardial ischemia developed during said (PTCA) balloon angioplasty.

4. The method of claim 3 wherein the parameter monitoring step comprises the steps of:
   A. detecting the arterial pressure, P, of the subject and generating in response thereto a blood pressure signal having a waveform in accordance with the detected arterial pressure;
   B. differentiating said blood pressure signal to produce a dP/dt signal having a waveform varying in accordance with the rate at which the blood pressure signal varies;
   C. detecting the peak of said dP/dt signal to determine the peak dP/dt;
   D. determining a value which is substantially equal to the arterial pressure at the time of said peak dP/dt; and
   E. dividing said latter value by said peak dP/dt signal, which thereby produces a measurement of the parameter corresponding to the systemic vascular resistance of said subject's cardiovascular system.

5. A method for monitoring the onset of painless myocardial ischemia in a resting patient comprising the steps of
monitoring a parameter corresponding to systemic vascular resistance of the patient, and
detecting when the parameter being monitored changes above or below a predetermined base line value as an indication that a myocardial ischemic change in the patient has occurred.

6. The method of claim 5 wherein the parameter monitoring step comprises the steps of:
   A. detecting the arterial pressure, P, of the patient and generating in response thereto a blood pressure signal having a waveform in accordance with the detected arterial pressure;
   B. differentiating said blood pressure signal to produce a dP/dt signal having a waveform varying in accordance with the rate at which the blood pressure signal varies;
   C. detecting the peak of said dP/dt signal to determine the peak dP/dt;
   D. determining a value which is substantially equal to the arterial pressure at the time of said peak dP/dt; and
   E. dividing said latter value by said peak dP/dt signal, which thereby produces a measurement of the parameter corresponding to the systemic vascular resistance of said patient's cardiovascular system.

7. A method for monitoring the onset of myocardial ischemia during a stress condition in a patient comprising the steps of
   monitoring a parameter value corresponding to the systemic vascular resistance of the subject, and
   detecting when said parameter value increases a selected amount of determining the onset of the myocardial ischemic event during said stress condition.

8. The method of claim 7 wherein said monitoring step comprises the steps of:
   A. detecting the arterial pressure, P, of the subject and generating in response thereto a blood pressure signal having a waveform in accordance with the detected arterial pressure;
   B. differentiating said blood pressure signal to produce a dP/dt signal having a waveform varying in accordance with the rate at which the blood pressure signal varies;
   C. detecting the peak of said dP/dt signal to determine the peak dP/dt;
   D. determining a value which is substantially equal to the arterial pressure at the time of said peak dP/dt; and
   E. dividing said latter value by said peak dP/dt signal, which thereby produces a measurement of the parameter value corresponding to the systemic vascular resistance of said subject's cardiovascular system.

9. A method for determining the drug dose level for inhibiting myocardial ischemic events in a subject comprising the steps of:
   monitoring a parameter value corresponding to the systemic vascular resistance of the subject,
   recognizing the time of myocardial ischemic event by a selected increase in value of said monitored parameter, and
   increasing the subject drug level in response to said selected increase in the monitored parameter value.

10. The method of claim 9 wherein the monitoring step comprises the steps of:
    A. detecting the arterial pressure, P, of the subject and generating in response thereto a blood pressure signal having a waveform in accordance with the detected arterial pressure;
    B. differentiating said blood pressure signal to produce a dP/dt signal having a waveform varying in accordance with the rate at which the blood pressure signal varies;
    C. detecting the peak of said dP/dt signal to determine the peak dP/dt;
    D. determining a value which is substantially equal to the arterial pressure at the time of said peak dP/dt; and
    E. dividing said latter value by said peak dP/dt signal, which thereby produces a measurement of the parameter value corresponding to the systemic vascular resistance of said subject's cardiovascular system.

11. A method for continuously determining systemic vascular resistance and cardiac output of a patient comprising the steps of
    A. generating values of a parameter corresponding to systemic vascular resistance of the patient by a first method;
    B. determining the systemic vascular resistance of the patient at two operating conditions using a method other than that of step A above; and
    C. calibrating said determining method of step A for providing a one-to-one reading of the thus calibrated parameter and said systemic vascular resistance.

12. The method of claim 11 wherein the generating step comprises the steps of:
    A. detecting the arterial pressure, P, of the patient and generating in response thereto a blood pressure signal having a waveform in accordance with the detected arterial pressure;
    B. differentiating said blood pressure signal to produce a dP/dt signal having a waveform varying in accordance with the rate at which the blood pressure signal varies;
    C. detecting the peak of said dP/dt signal to determine the peak dP/dt;
    D. determining a value which is substantially equal to the arterial pressure at the time of said peak dP/dt; and
    E. dividing said latter value by said peak dP/dt signal, which thereby produces a measurement of the parameter value corresponding to the systemic vascular resistance of said patient's cardiovascular system.

13. The method of claim 12 further comprising the step of
    determining cardiac output from said measurement corresponding to systemic vascular resistance.